US006421854B1

(12) United States Patent
Heimbrock

(10) Patent No.: US 6,421,854 B1
(45) Date of Patent: Jul. 23, 2002

(54) IMAGING STRETCHER

(75) Inventor: Richard H. Heimbrock, Cincinnati, OH (US)

(73) Assignee: Hill-Rom Services, Inc., Batesville, ID (US)

( * ) Notice: Subject to any disclaimer, the term of this patent is extended or adjusted under 35 U.S.C. 154(b) by 0 days.

(21) Appl. No.: 09/507,500

(22) Filed: Feb. 18, 2000

(51) Int. Cl.⁷ ............................................... A61G 13/04
(52) U.S. Cl. ...................... 5/610; 5/86.1; 5/600; 5/601; 5/611; 5/614; 280/43.17
(58) Field of Search ............................ 5/610, 611, 601, 5/600, 614, 86.1; 296/20; 280/43.17

(56) References Cited

U.S. PATENT DOCUMENTS

| 2,217,783 A | 10/1940 | Bell |
| 2,707,137 A | 4/1955 | Hollstein |
| 2,794,694 A | 6/1957 | Fullwood et al. |
| 3,302,022 A | 1/1967 | Brenner et al. |
| 3,397,411 A | 8/1968 | Rossi |
| 3,814,414 A | 6/1974 | Chapa |
| 3,840,221 A | 10/1974 | Hogan |
| 4,231,124 A | 11/1980 | Croxton |
| 4,489,449 A | 12/1984 | Failor et al. |
| 4,586,492 A | 5/1986 | Manahan |
| 4,653,482 A | 3/1987 | Kurland |
| 4,671,728 A | 6/1987 | Clark et al. |
| 4,698,837 A | 10/1987 | Van Steenburg |
| 4,723,808 A | 2/1988 | Hines ........................ 296/20 |

(List continued on next page.)

FOREIGN PATENT DOCUMENTS

| DE | 299 18 805 U1 | 10/1999 |
| EP | 0846457 A2 | 6/1998 |
| EP | 1020170 A2 | 7/2000 |
| WO | 98/35643 | 8/1998 |
| WO | 99/03418 | 1/1999 |
| WO | PCT/0140005 | 2/2001 |

OTHER PUBLICATIONS

Nesbit Evans Timetable (model 150000).
Stryker Visual Imaging Platform (model 974).
Stryker Fluoroscopy Stretcher (model 1075).
Hausted Legacy Fluoro-Track.
US Imaging V.A.C.S. Table (model 9650).

*Primary Examiner*—Alexander Grosz
(74) *Attorney, Agent, or Firm*—Barnes & Thornburg

(57) ABSTRACT

A stretcher includes an elongated base having a head end and a foot end, a plurality of floor-engaging casters rotatably mounted to the base, a radiolucent upper deck, head and foot end hydraulic cylinders coupled to the base adjacent to the head and foot ends thereof, and head and foot end connectors for coupling the head and foot end hydraulic cylinders to the head and foot ends of the upper deck. The head and foot end connectors secure the upper deck to the base while allowing (a) movement of the upper deck between a low position and a high position, (aa) translation of the upper deck toward the foot end of the base, and (aaa) rotation of the upper deck to a Trendelenberg position or to a reverse Trendelenberg position. The head end and foot end hydraulic cylinders are spaced apart to define a central imaging region above the base between the hydraulic cylinders which is free of structure that would interfere with imaging.

16 Claims, 9 Drawing Sheets

U.S. PATENT DOCUMENTS

| | | |
|---|---|---|
| 5,054,141 A | 10/1991 | Foster et al. |
| 5,063,624 A | 11/1991 | Smith et al. |
| 5,088,706 A | 2/1992 | Jackson |
| 5,131,103 A | 7/1992 | Thomas et al. .................. 5/601 |
| 5,131,105 A | 7/1992 | Harrawood et al. ............ 5/607 |
| 5,131,106 A | 7/1992 | Jackson .......................... 5/613 |
| 5,230,112 A | 7/1993 | Harrawood et al. ............ 5/607 |
| 5,450,639 A | 9/1995 | Weismiller et al. ............. 5/600 |
| 5,520,091 A | 5/1996 | Chromik ......................... 5/614 |
| 5,613,254 A | 3/1997 | Clayman et al. ................ 5/600 |
| 5,613,255 A | 3/1997 | Bish et al. |
| 5,621,933 A | 4/1997 | Knapp et al. |
| 5,675,851 A | 10/1997 | Feathers |
| 5,678,263 A | 10/1997 | Berthe ............................ 5/600 |
| 5,806,111 A * | 9/1998 | Heimbrock et al. ............ 5/600 |
| 5,839,136 A | 11/1998 | Vance et al. |
| 6,016,580 A | 1/2000 | Heimbrock et al. ............ 5/610 |
| 6,249,579 B1 * | 6/2001 | Hanson et al. .................. 5/611 |

* cited by examiner

IMAGING STRETCHER

BACKGROUND AND SUMMARY OF THE INVENTION

The present invention generally relates to a hospital stretcher. More particularly, the present invention relates to an imaging stretcher which lends itself to fluoroscopy imaging.

Fluoroscopy imaging with a C-Arm is used by caregivers for diagnostic and surgical visualization. Many conventional imaging tables have designs based on operating room tables. Often these tables are of a cantilever design where the support surface extends out from a single support column. Such tables usually have all electric controls, are relatively large and heavy, and are also expensive. Typically, a room having an operating room-type table is set up in a medical facility, and a C-Arm is temporarily brought into the room when needed for fluoroscopic observations.

Due to increase in the number of outpatient centers and clinics, especially pain management clinics, a need has arisen for a low cost, transportable imaging stretcher. In pain management procedures, the patient is placed on a support surface in a prone position and a nerve-deadening solution is injected from a needle to precise areas of the spine. Fluoroscopy imaging with a C-Arm is used to determine the location of the needle in the patient during such procedures. The C-Arm must be positioned to visualize specific places on the spine which requires the C-Arm to be moved between the neck and the lower back of a patient resting on a support surface, tilted to odd angles, and rotated from a vertical to a horizontal orientation without obstruction from the surface supporting the patient. Caregivers will appreciate a low cost imaging stretcher which includes an unobstructed X-ray window from the tailbone to the head of a patient resting on the support surface, with the ability to angle and maneuver the C-Arm around and under the patient.

There are some stretchers on the market today that have a radiolucent top that can be used for C-Arm procedures, but have a relatively wide surface with metal structure down the sides that interfere with rotating the C-Arm and shooting an image horizontally or diagonally through a patient. Some of these stretchers have an upper deck or a litter that slides end to end to achieve a large X-ray window, but they do not slide far enough so that the C-Arm can position under the head of a patient supported on the litter, and shoot an image diagonally through the neck without having to pull the C-Arm out from under the patient. Also in these stretchers, the C-Arm cannot be moved from the head to the lower back without obstruction. Some of these stretchers have a C-shaped base that allows C-Arm access from one side only.

An imaging stretcher according to the present invention includes a base having a head end and a foot end, an upper deck formed from a radiolucent material, and actuators coupled to the base adjacent to the head end and the foot end of the base respectively for movably supporting the upper deck. According to one aspect of the invention, the head end and foot end actuators are spaced wide apart to define a central imaging region above the base which is free of any components that would interfere with fluoroscopic imaging of a patient supported on the upper deck.

According to another aspect of the invention,. the head end and foot end actuators are coupled to the upper deck such that the upper deck is movable toward the foot end of the base. According to a further aspect of the invention, the upper deck may be unlocked, moved to a desired position and locked in place. According to still another aspect of the invention, movement of the upper deck toward the foot end of the base locates the head of a patient supported on the deck between the head end and foot end actuators in the central imaging region. According to a further aspect of the invention, a portion of the base extending between the head end and foot end actuators is formed to be closer to the floor than the end sections thereof supporting the casters to provide more clearance between the upper deck and the base between the actuators in the central imaging region.

According to another aspect of the invention, the upper deck is movable between a lowered position and a raised position, and pivotable between a first position where the foot end of the upper deck is raised above the head end thereof (also known as Trendelenberg position) and a second position where the head end of the upper deck is raised above the foot end thereof (also known as reverse Trendelenberg position).

According to still further aspect of the invention, the upper deck is formed to include a cutout adjacent to the head end thereof to provide space for a patient's face lying in a prone position on the upper deck. According to another aspect of the invention, the upper deck is formed to include a pair of openings adjacent to first and second sides thereof for supporting a pair of removable siderails. According to still another aspect of the invention, the upper deck is formed to include a plurality of handles which are also made of radiolucent material. According to a further aspect of the invention, the cutout, the openings for the siderails and the handles are all integrally molded with the upper deck.

According to another aspect of the invention, an elongated shaft having a longitudinal axis is coupled to the base for movement along the longitudinal axis. A foot pedal is movably mounted to the base adjacent to the foot end, and is configured to engage a portion of the shaft adjacent to the foot end to move the shaft toward the head end and cause the head end actuator to adjust the elevation of the head end of the upper deck. According to yet another aspect of the invention, the shaft is mounted to the base for rotation about the longitudinal axis between a first orientation and a second orientation. A steering wheel is coupled to the shaft for movement relative to the base between a first position spaced apart from the floor when the shaft is rotated to the first orientation and a second position engaging the floor when the shaft is rotated to the second orientation.

Additional features of the present invention will become apparent to those skilled in the art upon a consideration of the following detailed description of the preferred embodiments exemplifying the best mode of carrying out the invention as presently perceived.

BRIEF DESCRIPTION OF THE DRAWINGS

The detailed description particularly refers to the accompanying figures in which:

FIG. 7 is a sectional view along the line 7—7 in FIG. 5, and showing the steering wheel support assembly movably coupled to the siderails, and disposed in a raised position spaced apart from the floor, FIG. 8 is a sectional view similar to FIG. 7, and showing the steering wheel support assembly in a lowered, floor-engaging position.

DETAILED DESCRIPTION OF THE DRAWINGS

Figure 1:
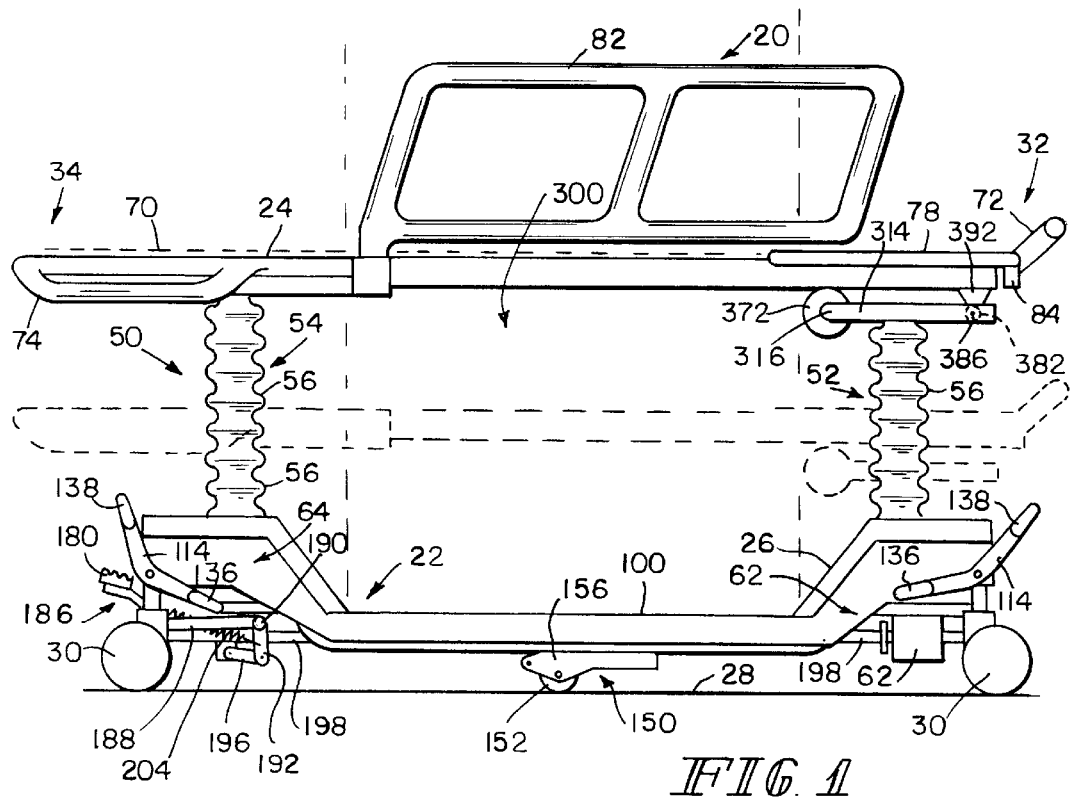
FIG. 1 is a side view of an imaging stretcher according to the present invention, showing a relatively narrow upper deck supported above a relatively low profile base by a pair of hydraulic cylinders which are spaced wide apart to form a central imaging region free of any non-radiolucent components, the upper deck being mounted to the base for movement toward the foot end of the stretcher, and further showing in phantom the upper deck in a lowered position.

Although the term "stretcher" is used throughout the specification, it is understood that the novel features of the invention may be incorporated into any type of a patient support device—such as a hospital bed or an operating table. Also, although the term "fluoroscopy" is used throughout the specification for convenience, it will be construed to include any other type of imaging. Also the terms "hydraulic pump" or "hydraulic cylinder" or "hydraulic pump/cylinder assembly" will be construed to include any hydraulic, pneumatic, mechanical or electrical device for lifting, lowering or tilting the upper deck. In other words, the features of the present invention are not to be limited to the use with a stretcher or a fluoroscope or a hydraulic device.

Referring to FIGS. 1–4, a stretcher 20 in accordance with the present invention includes a low profile base 22 with a relatively large wheelbase, a relatively narrow slidably-mounted upper deck 24 coupled to the base 22, a protective shroud 26 covering the base 22, a head end 32, a foot end 34, an elongated first side 36, an elongated second side 38 and a longitudinal axis 40. As used in this description, the phrase "head end 32" will be used to denote the end of any referred-to object that is positioned to lie nearest the head end 32 of the stretcher 20, and the phrase "foot end 34" will be used to denote the end of any referred-to object that is positioned to lie nearest the foot end 34 of the stretcher 20. Likewise, the phrase "first side 36" will be used to denote the side of any referred-to object that is positioned to lie nearest the first side 36 of the stretcher 20 and the phrase "second side 38" will be used to denote the side of any referred-to object that is positioned to lie nearest the second side 38 of the stretcher 20.

Figure 13:
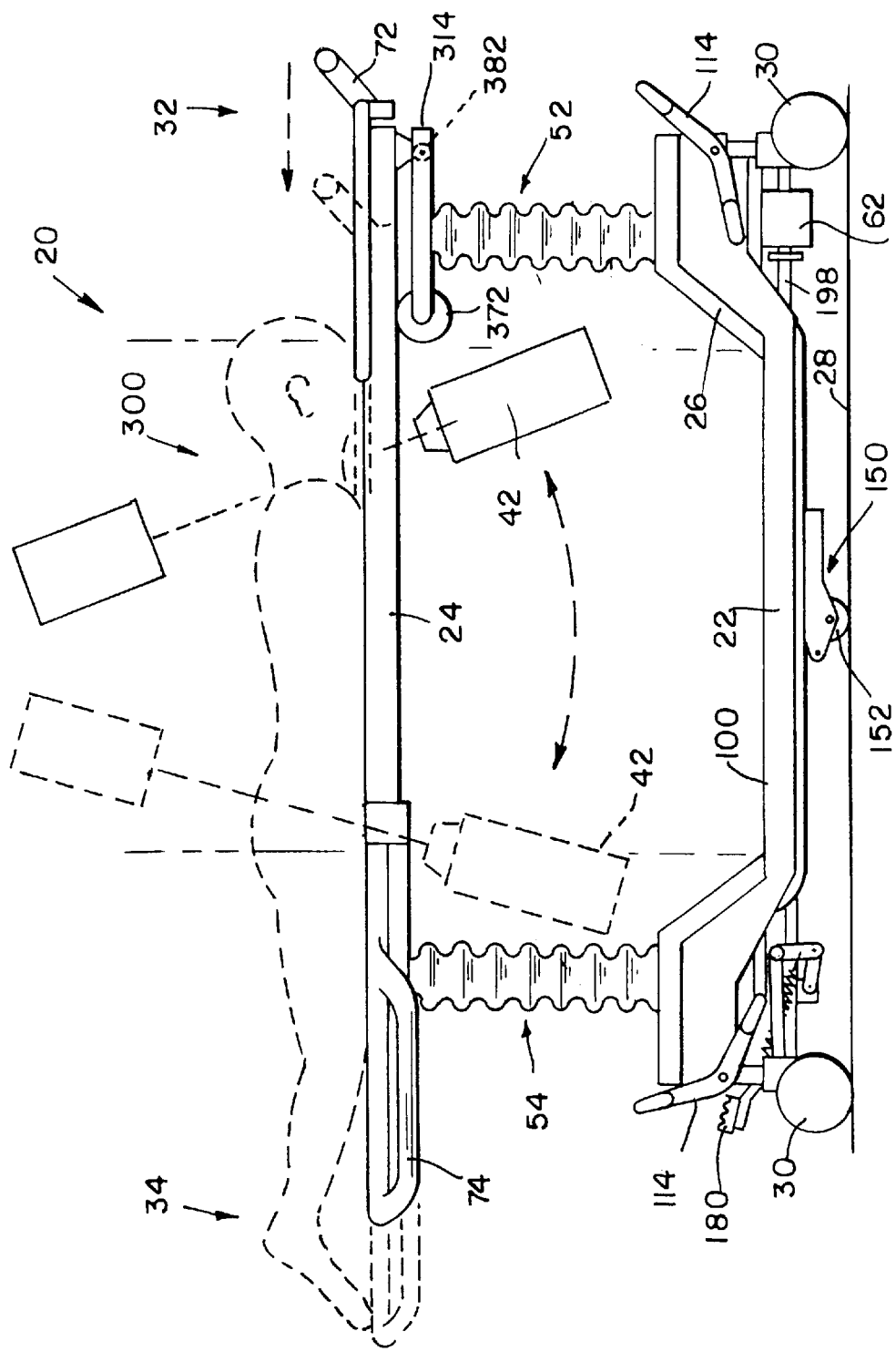
FIG. 13 is a side view similar to FIG. 1, showing in dotted lines the upper deck slid toward the foot end of the stretcher, and further showing in solid lines the C-Arm positioned adjacent to the head of a patient supported on the upper deck and tilted about a transversely-extending axis to shoot an image diagonally through the neck, and further showing in phantom lines the C-Arm positioned adjacent to the lower back of the patient and tilted to shoot an image diagonally through the tailbone.

The upper deck 24 is formed from a radiolucent material—end to end and side to side—to facilitate fluoroscopic observations of a patient supported on the upper deck 24—for example, for conducting pain management procedures. The stretcher 20 is particularly suitable for use in endoscopy, cardiac catheterization, and other procedures requiring fluoroscopy. As shown in FIG. 13, the deck 24 is movable toward the foot end 34 of the stretcher 20 so that a C-Arm 42 can position under the head of a patient supported on the upper deck 24 and tilted about a transversely-extending axis to shoot an image diagonally through the neck of the patient without pulling the C-Arm out from under the patient. Relatively narrow upper deck 24 (about 20 inches or 50 centimeters wide) allows the C-Arm 42 to rotate about a longitudinally-extending axis from a vertical orientation to a horizontal orientation, as shown in FIG. 14, to shoot an image horizontally through the head of a patient supported on the upper deck 24 without interference from siderails—particularly non-removable metal siderails.

The base 22 is supported on floor 28 by four caster assembles 30 to allow the stretcher 20 to be rolled over the floor 28 to transport a patient. The upper deck 24 is movably supported above the base 22 by a lifting mechanism 50 in order to raise, lower, and tilt the upper deck 24 relative to the base 22. Illustratively, the upper deck lifting mechanism 50 includes head end and foot end hydraulic cylinders 52 and 54 covered by flexible boots 56. The hydraulic cylinders 52, 54 (sometimes referred to herein as the actuators) are spaced wide apart (about 60 inches or 150 centimeters) to provide room for maneuvering the C-Arm 42. The hydraulic cylinders 52, 54 are coupled to respective hydraulic pumps 62 and 64 supported on the base 22. The head end hydraulic cylinder 52 controls the vertical position of the head end 32 of the upper deck 24 relative to the base 22, and the foot end hydraulic cylinder 54 controls the vertical position of the foot end 34 of the upper deck 24 relative to the base 22. The hydraulic cylinders 52, 54 adjust the vertical position of the upper deck 24 between a low position (about 24 inches or 60 centimeters above the floor) to facilitate patient egress and ingress, and a high position (about 40 inches or 102 centimeters above the floor) to provide a comfortable position for a Surgeon standing next to a patient supported on the upper deck 24. In addition, the hydraulic cylinders 50, 52 tilt the upper deck 24 to one of three positions—a flat, horizontal position shown in FIG. 1, a Trendelenburg position shown in FIG. 2 where a patient's feet are raised above the patient's head, or a reverse Trendelenburg position shown in FIG. 3 where the patient's head is raised above the patient's feet.

Figure 14:
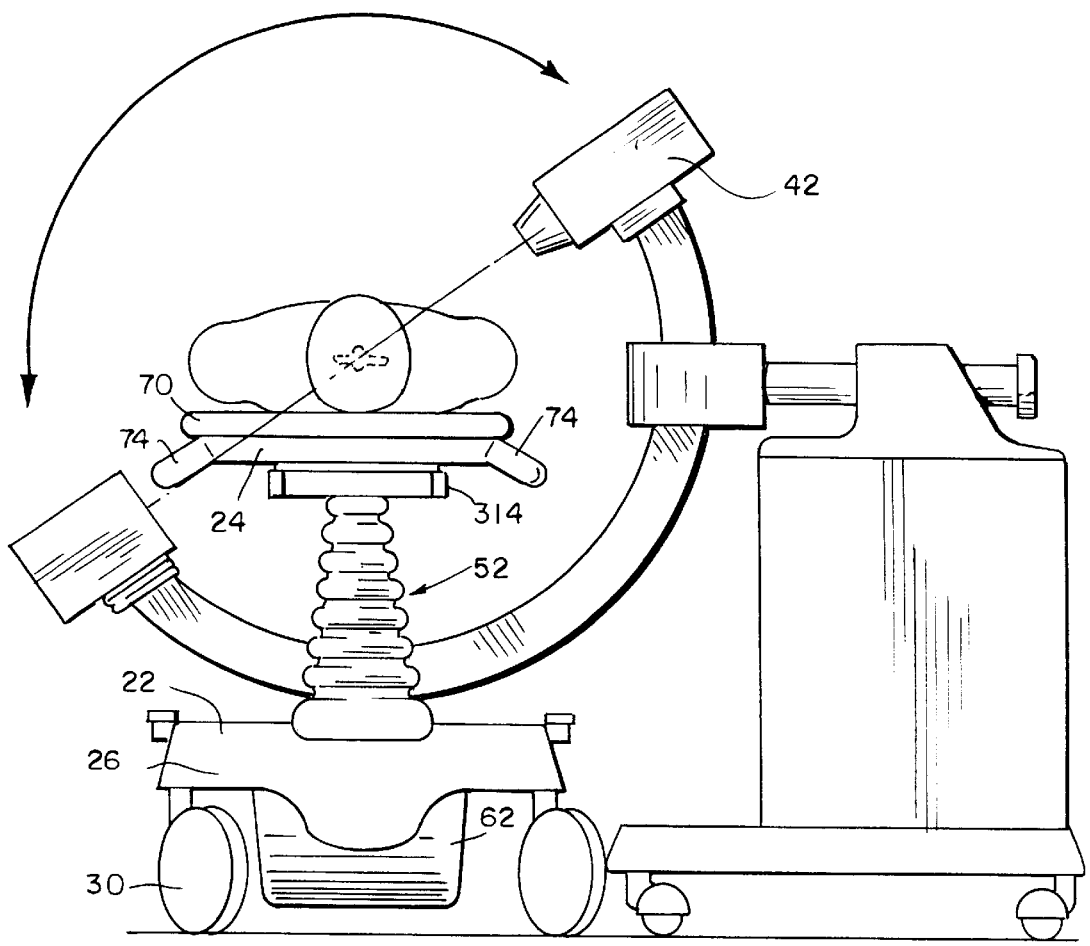
FIG. 14 is an end view of the stretcher, showing the C-Arm rotated about a longitudinally-extending axis to shoot an image through the head of a patient supported on the upper deck without interference from siderails or any other metal structures in the imaging region.

A mattress pad 70 may be disposed on the upper deck 24 for supporting a patient as shown in FIGS. 1 and 14. The mattress pad 70 may include selectively activated, inflatable bladders to provide special support that may be required for certain medical procedures—such as imaging a patient's spine when the patient is lying in a prone position on the deck 24, for example, for pain management procedures. The upper deck 24 is configured to form a raised, gently-curved push handle 72 near the head end 32 of the stretcher 20, and two downwardly-sloping side handles 74 near the foot end 34 adjacent to the two sides 34, 36 of the stretcher 20 as shown in FIGS. 1–4. A caregiver can grip either the head end push handle 72 or the two foot end side handles 74 to maneuver the stretcher 20 over the floor 20. After unlocking the upper deck 24, the caregiver may use the head end push handle 72 or the foot end side handles 74 to move the upper deck 24 to a desired position, and then lock the upper deck 24 in place. As indicated, the caregiver may wish to move the upper deck 24 to a different position to view a different portion of a patient's body for a diagnostic or a surgical procedure. The ergonomic designs of the handles 72, 74 provide a comfortable grip.

Figure 4:
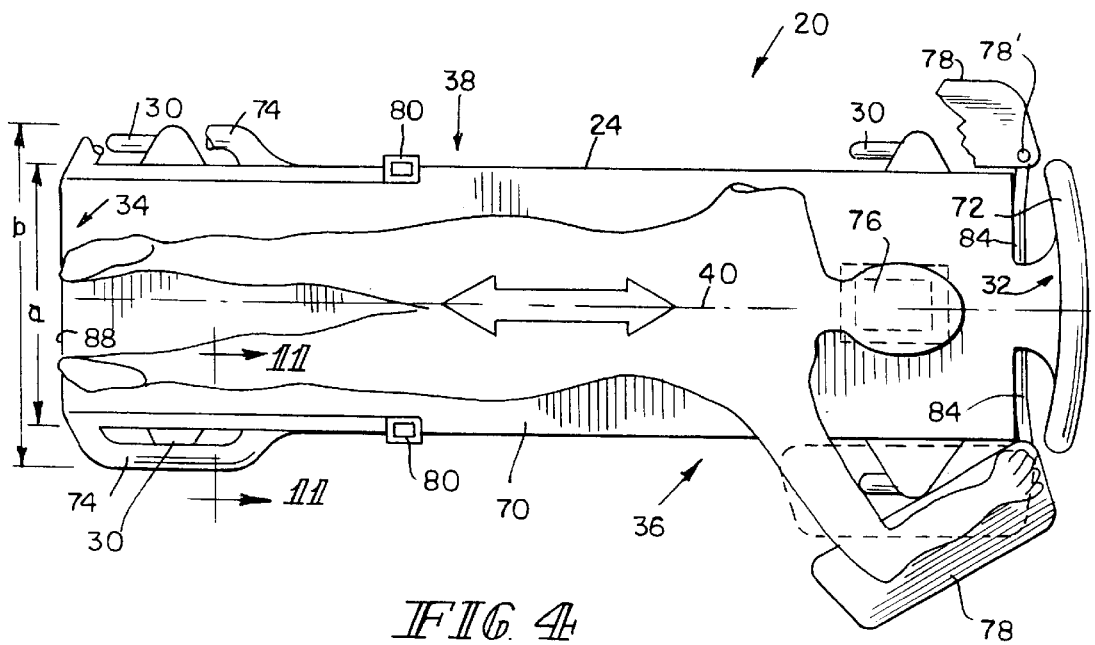
FIG. 4 is a plan view of the stretcher of FIGS. 1–3, showing the upper deck formed to include a push handle near the head end, a pair of downwardly-sloping side handles near the foot end, a cutout near the head end to provide space for a patient's face lying in a prone position on the upper deck, a pair of armboards pivotally coupled near the head end of the upper deck for supporting a patient's arms, a pair of openings adjacent to the two sides of the upper deck for removably receiving a pair of siderails, and a cross bar near the head end of the upper deck for supporting one or more IV poles.
Figure 15:
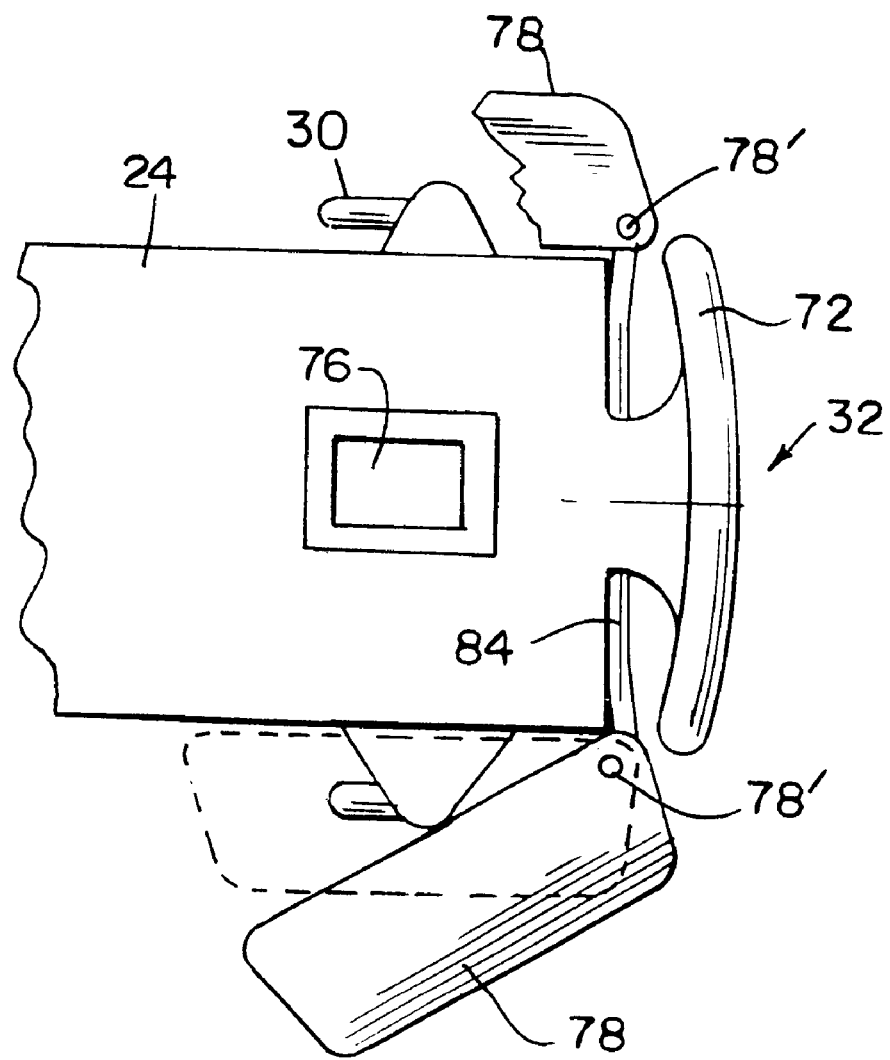
FIG. 15 is a plan view similar to FIG. 4, showing the upper deck formed to include a cutout near the head end to provide space for a patient's face lying in a prone position on the upper deck.

As shown in FIGS. 4 and 15, a cutout 76 is formed in the upper deck 24 to provide space for a patient's face lying in a prone position on the upper deck 24. In accordance with one aspect of the present invention, the stretcher 20 is configured such that the cutout 76 is located between the hydraulic cylinders 52, 54 in an X-ray window 300 when the deck 24 is moved toward the foot end 34 of the stretcher 20 to facilitate shooting an image diagonally through the neck of the patient as shown in FIG. 13. A transversely-extending cross bar 84 is secured to the upper deck 24 near the head end 32 of the stretcher 20. In accordance with another aspect of the present invention, an armboard 78 is pivotally coupled to each end of the cross bar 84 by a pivot pin 78' adjacent to the two sides 34, 36 for movement between a first position extending toward the foot end and a second position extending away from the foot end for supporting a patient's arms. Pivoting armboards 78 allow prone patients to position their arms over their heads and still be supported by the armboards 78 as shown in FIG. 4. The upper deck 24 is further configured to form openings 80 adjacent to the two sides 34, 36 for removably receiving a pair of plug-in siderails 82 as shown in FIG. 1. The removable siderails 82 allow shooting an image diagonally through the head or the tailbone of a patient supported on the upper deck 24 without interference from the siderails 82 as shown in FIG. 14. One or more IV poles may be secured to the cross bar 84 near the head end 32 of the stretcher 20 for holding solution containers or other objects at a position elevated above the upper deck 24. The foot end portion 88 of the upper deck 24 may be angled away from the upper deck 24 to provide comfortable ankle support for a patient lying in a prone position on the upper deck 24. Illustratively, the upper deck 24 is molded from a radiolucent foam plastic material and provided with fiber glass outer shell. The handles 72, 74, the cutout 76 and the siderail openings 80 may all be integrally molded with the upper deck 24.

The combination of a relatively narrow deck (about 20 inches or 50 centimeters), a high position of the deck 24 when raised to a full height (about 40 inches or 102 centimeters above the floor) and widely spaced-apart hydraulic cylinders 52, 54 (about 60 inches or 150 centimeters) can cause instability. Stability is very important during these types of procedures, and the litter 24 must not wobble. Also, the litter 24 must be stable for a patient to get on and off. Typically, OR tables (Operating Room tables) have a very heavy base to add stability. A heavy base is not acceptable on fluoroscopic-type stretchers that have some intention of being transportable. A wide wheelbase (about 24 inches or 60 centimeters) is therefore desired for stability along with a narrow top (about 20 inches or 50 centimeters) to allow rotation of the C-arm 42 about a longitudinally-extending axis as shown in FIG. 14. However, the caster assemblies 30 or the brake-steer pedals 114 cannot protrude farther out than the upper deck 24 as it creates a trip hazard if walking around the stretcher 20. In accordance with an aspect of the present invention, the side handles 74 and the armboards 78 extend outwardly from the deck 24 beyond the caster assemblies 30 and the brake-steer pedals 114 coupled to the base 22. Thus, the caster assemblies 30 and the brake-steer pedals 114 remain within the footprint of the upper deck 24, the side handles 74 and the armboards 78.

Figure 5:
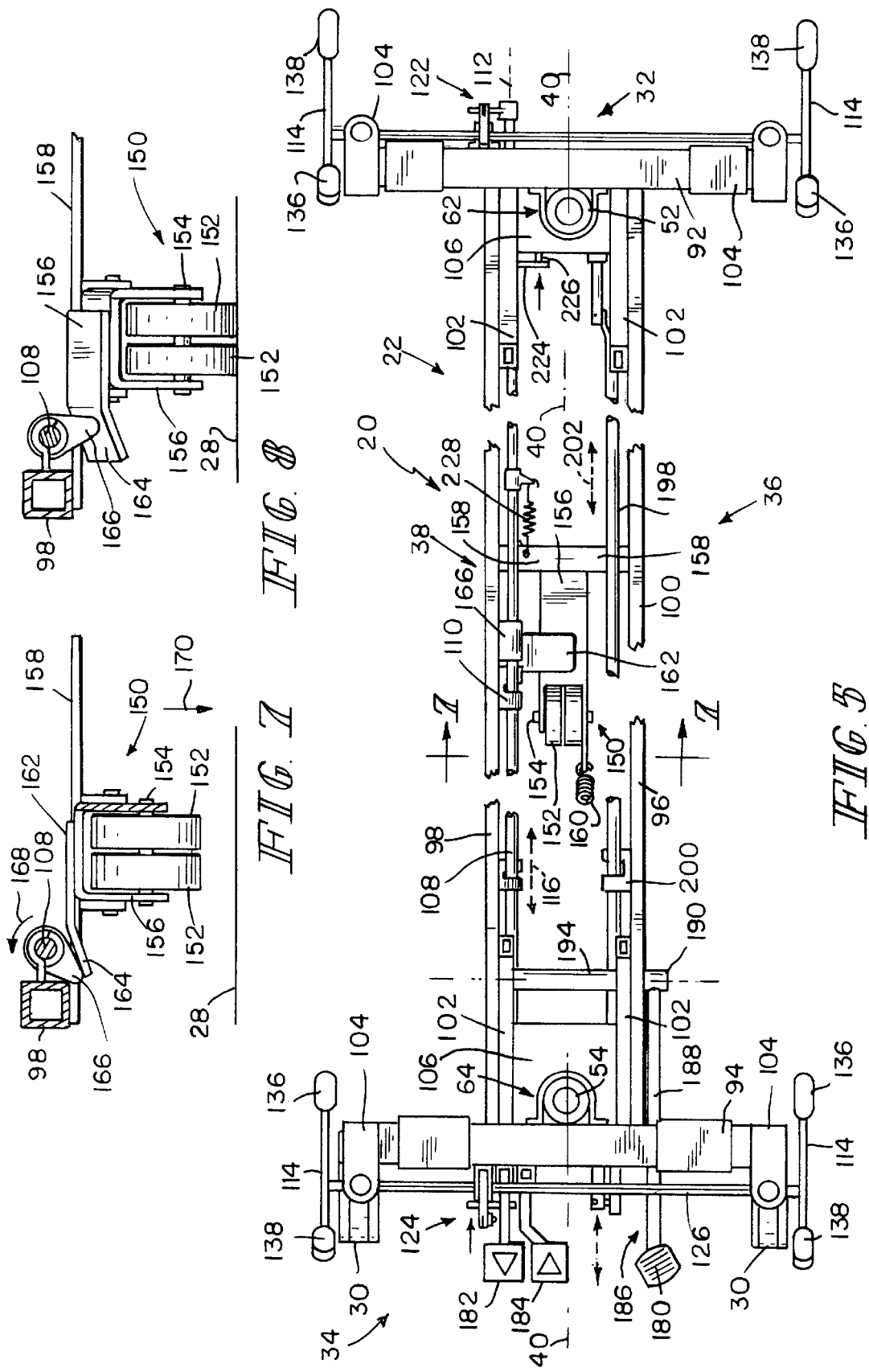
FIG. 5 is a plan view of the stretcher chassis without the upper deck and without a shroud covering the base, the base including two cross members held in longitudinally spaced apart relationship by two longitudinally-extending, laterally-spaced siderails, a caster assembly coupled to each end of the two cross members, a cross plate attached to the two siderails at each end for supporting head end and foot end hydraulic pump/cylinder assemblies, a steering wheel support assembly movably coupled to the two siderails intermediate of the two cross members, a longitudinally-extending, slidably-mounted brake-steer shaft coupled to the steering wheel support assembly, a brake-steer butterfly pedal pivotally mounted at each end of the two cross members, head end and foot end pressure release pedals movably coupled to the base near the foot end, a foot pump pedal mounted to the base near the foot end and coupled to hydraulic pumps for pumping fluid into the hydraulic cylinders.

As shown in FIG. 5, the base 22 includes a head end cross member 92 and a foot end cross member 94. The head end and foot end cross members 92, 94 are held in longitudinally spaced apart relationship by two longitudinally-extending, laterally-spaced siderails 96 and 98 secured to downwardly-extending brackets (not shown) fixed to the cross members 92, 94. The two longitudinally-extending siderails 96, 98 have step-down middle portions 100 that are configured to be closer to the floor 28 (about 4 inches or 10 centimeters from the floor 28) than their respective end portions (about 13 inches or 33 centimeters from the floor 28). The step-down middle portions 100 of the base 22 provides more vertical clearance between the base 22 and the upper deck 24 between the two hydraulic cylinders 52, 54 in the central imaging region 300 for the C-Arm 42. High end portions of the base 22, on the other hand, allow use of larger caster assemblies 30. A short end section 102 is attached at each end of the two siderails 96, 98 to lend rigidity to the structure. Coupled to each end of the two cross members 92, 94 is an outwardly-extending right angle bracket 104. Each right angle bracket 104 supports a caster assembly 30 and a brake-steer butterfly pedal 114. A cross plate 106 is attached to the two siderails 96, 98 near the head end 32 of the base 22 to support the head end hydraulic cylinder/pump assembly 52/62. Likewise, another cross plate 106 is attached to the two siderails 96, 98 near the foot end 34 of the base 22 to support the foot end hydraulic cylinder/pump assembly 54/64. The cross members 92, 94, the siderails 96, 98 and short end sections 102 are in the form of extruded tubes having a square cross section, and made from rigid high strength, light weight materials—such as steel or aluminum.

A longitudinally-extending brake-steer shaft 108 is slidably and rotatably mounted to the siderail 98 near the second side 38 of the base 22 by a plurality of brackets 110 as shown in FIG. 5. The brake-steer shaft 108 rotates about its longitudinal axis 112 in either direction in response to rotation of a brake-steer butterfly pedal 114, and is translatable in a longitudinal direction, indicated by a double-headed arrow 116, either toward or away from the foot end 34 in response to the operation of a head end pressure release pedal 182 coupled to the foot end 34 of the base 22. A linkage assembly 122 couples the brake-steer shaft 108 to two brake-steer pedals 114 at the head end 32 of the stretcher 20. Likewise, a linkage assembly 124 couples the brake-steer shaft 108 to two brake-steer pedals 114 at the foot end 34 of the stretcher 20. Since the two linkage assemblies 122, 124 are similar to each other, only the foot end linkage assembly 124 will be described.

Figure 6:
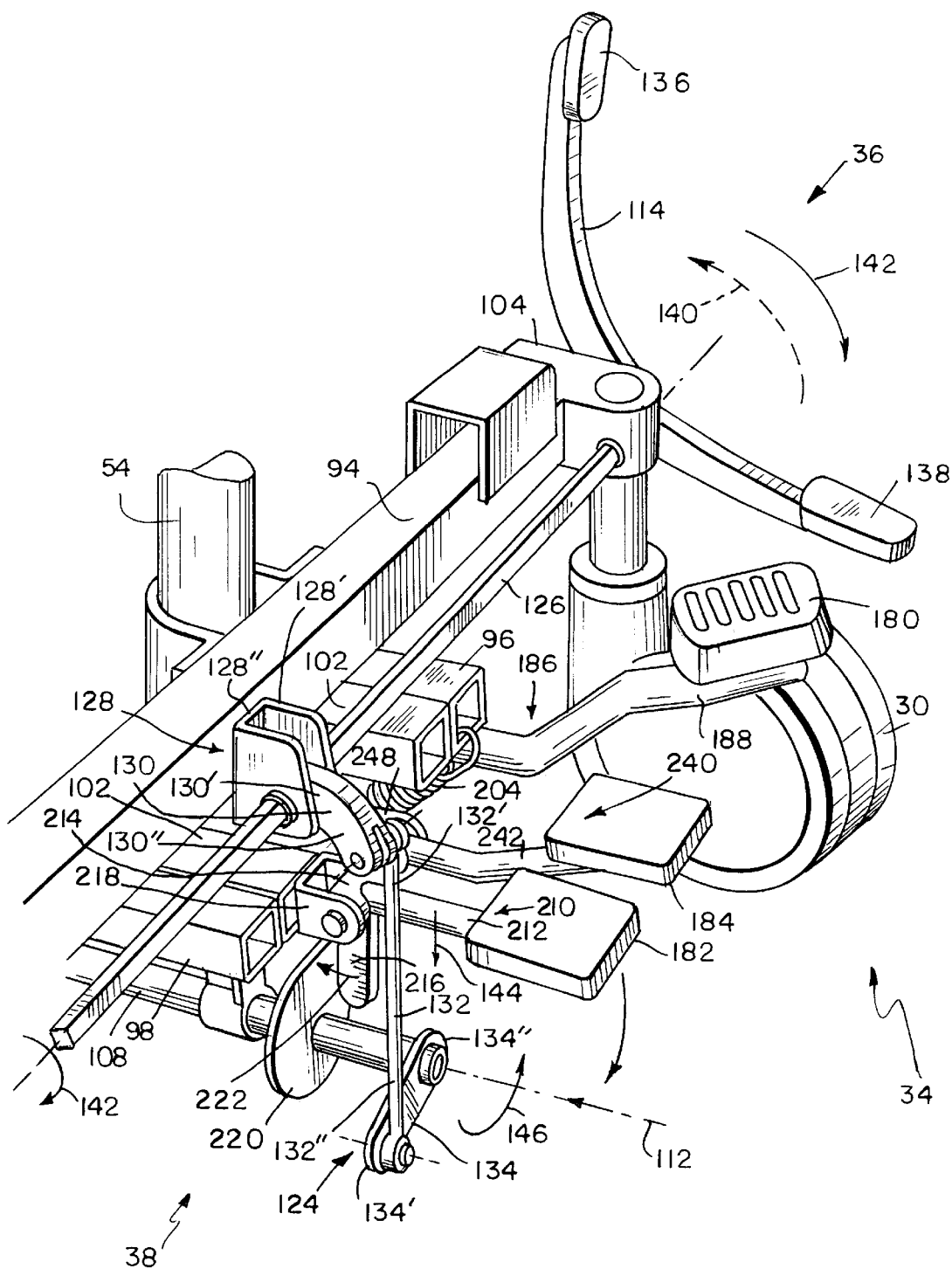
FIG. 6 is a perspective view of the foot end of the base, showing the foot end cross member, two longitudinally-extending siderails coupled to the cross member, a caster assembly coupled to one end of the cross member, a brake-steer butterfly pedal coupled to the brake-steer shaft, a pair of hydraulic pressure release pedals coupled to the foot end of the base, a linkage assembly coupling a head end pressure release pedal to the brake-steer shaft, and a foot pump pedal coupled to the base and coupled to the hydraulic pumps.

Referring to FIG. 6, the foot end linkage assembly 124 includes a cross shaft 126 having its ends rotatably supported by two outwardly-extending right angle brackets 104 coupled to the foot end cross member 94. Another bracket 128, having a C-configuration in plan view, supports the cross shaft 126 intermediate of the two right angle brackets 104. The bracket 128 includes two vertically-disposed side plates 128' held in laterally spaced apart relation by a crosswise back plate 128". The back plate 128" is fixed to the foot end cross member 94. A brake-steer pedal 114 is fixed to each end of the cross shaft 126. A bent link 130 has a first end 130' fixed to the cross shaft 126 between the two vertically-extending side plates 128' of the bracket 128, and a second end 130" pivotally coupled to a first end 132' of a connecting link 132. The second end 132" of the connecting link 132 is pivotally coupled to a first end 134' of a short link 134. A second end 134" of the short link 134 is fixed to the foot end 34 of the brake-steer shaft 108.

The brake-steer pedal 114 has three positions—(a) a generally horizontal neutral position, (aa) a braking position where a braking portion 136 of the brake-steer pedal 114 is angled downwardly and an opposite steering portion 138 of the brake-steer pedal 114 is angled upwardly, and (aaa) a steering position where the steering portion 138 of the brake-steer pedal 114 is angled downwardly and the braking portion 136 of the brake-steer pedal 114 is angled upwardly. When the brake-steer pedal 114 is generally horizontal, the caster assemblies 30 are free to swivel and rotate. From the generally horizontal neutral position, the caregiver can depress the braking portion 136 of the brake-steer pedal 114 in an anticlockwise braking direction indicated by arrow 140 in FIG. 6 to a braking position. Rotation of the brake-steer pedal 114 to the braking position moves brake shoes (not shown) into engagement with the caster assemblies 30 to lock the caster assemblies 30 in place.

From the braking position, the caregiver can depress the steering portion 138 of the brake-steer pedal 114 to rotate the brake-steer pedal 114 back to the horizontal neutral position. When the brake-steer pedal 114 is in the neutral position, the caregiver can depress the steering portion 138 of the brake-steer pedal 114 to rotate the cross shaft 126 in a clockwise steering direction indicated by arrow 142 in FIG. 6 to a steering position. Rotation of the cross shaft 126 to the steering position, causes the bent link 130 to also rotate in the clockwise direction 142 to, in turn, cause the connecting link 132 to move in a downwardly direction indicated by arrow 144 and cause the short link 134 and the brake-steer shaft 108 to rotate in an anticlockwise direction indicated by arrow 146 in FIG. 6. Rotation of the brake-steer shaft 108 in the anticlockwise direction 146 causes a steering wheel support assembly 150 to lower a pair of steering wheels 152 to engage the floor 28.

As shown in FIGS. 5, 7 and 8, the steering wheel support assembly 150 includes a shaft 154 having the wheels 152 (also referred to herein as center or steering wheels) mounted side-by-side thereon. The shaft 154 is fixed to the foot end 34 of an elongated wheel-mounting bracket 156. The head end 32 of the wheel-mounting bracket 156 is pivotally coupled to a cross plate 158 having its ends attached to the siderails 96, 98. The wheel-mounting bracket 156 is movable between a raised position shown in FIG. 7 where the steering wheels 152 are spaced apart from the floor 28, and a lowered position shown in FIG. 8 where the steering wheels 152 are in engagement with the floor 28. A vertically-extending spring 160 extends between the foot end 34 of the wheel-mounting bracket 156 and the siderail 96. The vertically-extending spring 160 normally biases the wheel-mounting bracket 156 to the raised position spaced apart from the floor 28. Fixed to the wheel-mounting bracket 156 is a transversely-extending cam plate 162 having a downwardly sloping end portion 164 extending toward the brake-steer shaft 108. The downwardly sloping end portion 164 of the cam plate 162 is configured for engagement with a cam 166 mounted on the brake-steer shaft 108. As explained above, rotation of the steer portion 138 of the brake-steer pedal 114 in the clockwise direction 142 to the steering position causes the brake-steer shaft 108 to rotate in the anticlockwise direction 146 shown in FIG. 6. Rotation of the brake-steer shaft 108 in the anticlockwise direction 146 causes the cam 166 fixed thereto to also rotate in an anticlockwise direction indicated by arrow 168 in FIG. 7. Rotation of the cam 164 to in the anticlockwise direction 168 displaces the wheel-mounting bracket 156 in a downward direction indicated by arrow 170, causing the steering wheels 152 to engage the floor 28 as shown in FIG. 8.

The upper deck lifting mechanism 50 includes a foot pump pedal 180, a head end pressure release pedal 182 and a foot end pressure release pedal 184 as shown in FIG. 6. The pedals 180-184 are pivotally coupled to the base 22 near the foot end 34 of the stretcher 20, and control the vertical movement of the head end 32 and the foot end 34 of the upper deck 24. From their generally horizontal operative positions shown in FIG. 6, the pressure release pedals 182, 184 can be flipped up to their respective, generally vertical out-of-the-way inoperative positions.

Figure 2:
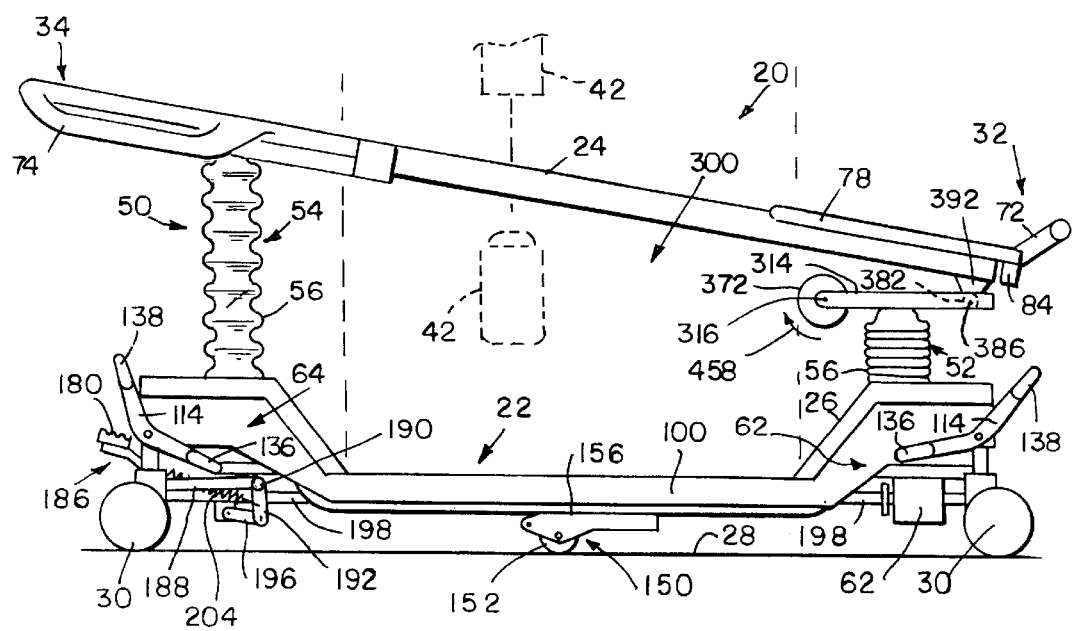
FIG. 2 is a side view similar to FIG. 1, showing the upper deck in a Trendelenberg position where a patient's feet are raised above the head.
Figure 3:
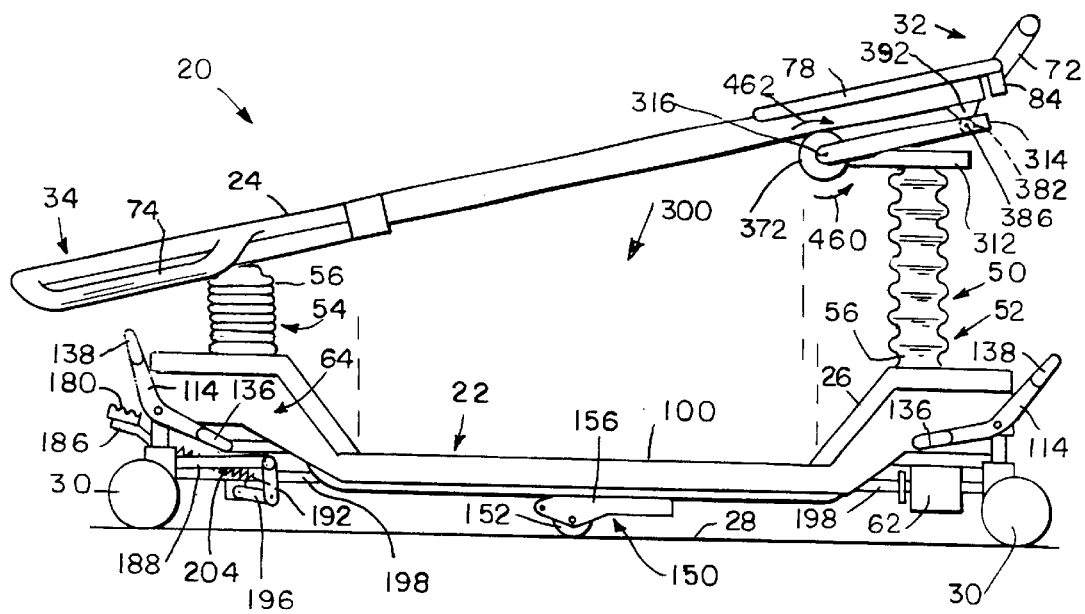
FIG. 3 is a side view similar to FIGS. 1 and 2, showing the upper deck in a reverse Trendelenberg position where a patient's head is raised above the feet.

Referring to FIGS. 1–3, 5 and 6, an actuating member 186 includes an outwardly-extending, generally horizontal portion 188, an intermediate base portion 190 and a downwardly-extending, generally vertical portion 192. The foot pump pedal 180 is fixed to the free end of the generally horizontal, outwardly-extending portion 188. As shown in FIG. 5, the base portion 190 of the actuating member 186 is attached to a cross shaft 194 rotatably coupled to the siderails 96, 98 near the foot end 34 of the stretcher 20. As shown in FIGS. 1–3, the free end of the generally vertical portion 192 of the actuating member 186 is coupled to the foot end 34 of a longitudinally-extending, reciprocally-mounted shaft 198 through a right angle member 196 such that vertical reciprocating motion of the foot pump pedal 180 causes horizontal reciprocating motion of the shaft 198. The longitudinally-extending shaft 198 is slidably mounted to the siderail 96 near the first side 36 of the stretcher 20 (on the side opposite from the longitudinally-extending brake-steer shaft 108) by a plurality of brackets 200 for movement toward and away from the foot end 34 of the stretcher 20 in a direction indicated by a double-headed arrow 202 in FIG. 5. The longitudinally-extending shaft 198 is coupled to the head end hydraulic pump 62 near the head end 32 of the stretcher 20 (FIGS. 1–3), and to the foot end hydraulic pump 64 near the foot end 34 of the stretcher 20. As shown in FIGS. 1–3 and 6, a generally horizontally-extending spring 204 is coupled between the free end of the generally vertical portion 192 and the foot end 34 of the siderail 96 to bias the foot pump pedal 180 upwardly to a generally-horizontal raised position shown in FIG. 6. From the generally-horizontal raised position, the caregiver can depress the foot pump pedal 180 to cause the longitudinally-extending shaft 198 to move toward the foot end 34 of the stretcher 20. Caregiver can then release the pressure on the foot pump pedal 180 to allow the generally horizontally-extending spring 204 to pull the longitudinally-extending shaft 198 away from the foot end 34 of the stretcher 20, and to lift the foot pump pedal 180 upwardly to the generally-horizontal raised position shown in FIG. 6. Caregiver can then again depress the foot pump pedal 180. Reciprocating motion of the shaft 198 causes the pumps 62, 64 to pump fluid into the hydraulic cylinders 52, 54 respectively to, in turn, cause the upper deck 24 to rise.

As shown in FIG. 6, an actuating member 210 includes an outwardly-extending, generally horizontal portion 212, an intermediate base portion 214 and a downwardly-extending, generally vertical portion 216. The head end pressure release pedal 182 is coupled to the free end of the generally horizontal portion 212. The base portion 214 of the actuating member 210 is pivotally coupled to a c-shaped bracket 218 mounted to the foot end 34 of the siderail 98 near the second side 38 of the stretcher 20. The free end of the downwardly-extending portion 216 is configured to engage a transverse plate 220 fixed on the brake-steer shaft 108 near the foot end 34 thereof From a generally horizontal position shown in FIG. 6, the caregiver can depress the head end pressure release pedal 182 to thereby cause the downwardly-extending portion 216 of the actuating member 210 to rotate in a clockwise direction indicated by arrow 222. Rotation of the generally vertical portion 216 in the clockwise direction 222 pushes the transverse plate 220 and the brake-steer shaft 108 coupled thereto toward the head end 32 of the stretcher 20. When the brake-steer shaft 108 moves toward the head end 32, a transversely-mounted actuator 224 coupled to the brake-steer shaft 108 depresses a pressure release pin or button 226 coupled to the head end hydraulic pump 62 as shown in FIG. 5 to release the pressure in the head end hydraulic cylinder 52 to, in turn, lower the head end 32 of the upper deck 24. As shown in FIG. 5, a generally horizontally-extending spring 228 coupled between the brake-steer shaft 108 and the siderail 98 biases the brake-steer shaft 108 to return to its original position when the pressure release pedal 182 is freed.

An actuating member 240 includes an outwardly-extending, generally horizontal portion 242, an intermediate base portion and a downwardly-extending, generally vertical portion. The foot end pressure release pedal 184 is coupled to the free end of the generally horizontal portion 242. The base portion of the actuating member 240 is pivotally coupled to a c-shaped bracket 248 mounted to the foot end 34 of the siderail 98 near the second side 38 of the stretcher 20. When the foot end pressure release pedal 1 84 is depressed, the free end of the downwardly-extending portion depresses a pressure release pin or button coupled to the foot end hydraulic pump 64 to release the pressure in the foot end hydraulic cylinder 54 to, in turn, lower the foot end 34 of the upper deck 24.

Referring to FIGS. 9–12, the head end 32 of the radiolucent upper deck 24 is coupled to the head end hydraulic cylinder 52 by a head end support assembly 302, and the foot end 34 of the deck 24 is coupled to the foot end hydraulic cylinder 54 by a foot end support assembly 304. As previously explained, the head end cylinder 52 controls a vertical position of the head end 32 of the upper deck 24, and the foot end cylinder 54 controls a vertical position of the foot end 34 of the upper deck 24. As shown in FIGS. 1–3, the head end and foot end support assemblies 302, 304 are spaced wide apart (about 60 inches or 150 centimeters) to define the central imaging region 300 above the base 22 between the head end and foot end hydraulic cylinders 52, 54 which is free of any metallic structures that would interfere with imaging. The two support assemblies 302, 304 (sometimes referred to herein as the head end and foot end connectors) secure the upper deck 24 to the base 22, while allowing translation of the upper deck 24 toward the foot end 34 of the stretcher 20 so that a C-Arm 42 can be positioned anyplace from the neck to the tailbone of a patient supported on the deck 24 or tilted to a suitable angle as shown in FIG. 13, or rotated from a vertical to a horizontal orientation as shown in FIG. 14 without any obstruction and without having to pull the C-Arm out from under the patient. For example, the C-Arm 42 can be located near the head end 32 of the stretcher 20 and tilted as shown in FIG. 13 to shoot an image diagonally through the neck of the patient.

Figure 9:
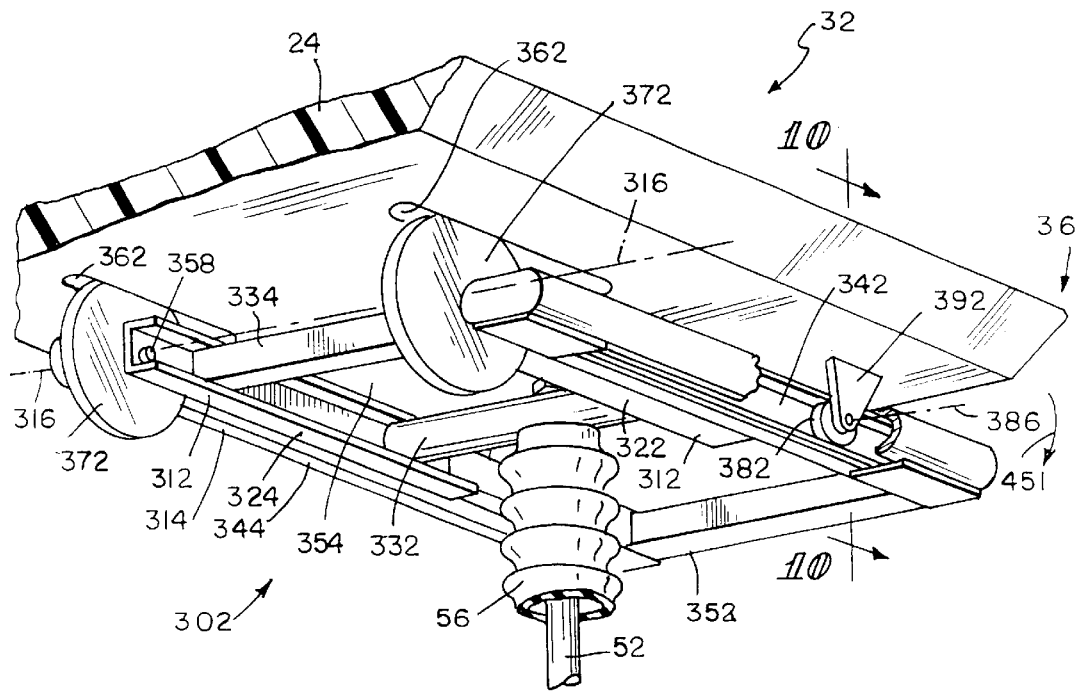
FIG. 9 is a perspective view showing a support assembly coupling the head end of the upper deck to the head end hydraulic cylinder, the head end support assembly including two generally rectangular frames nested within each other, the rectangular frames being pivotally coupled to each other near their respective foot ends by a pair of pivot pins for rotation about a transversely-extending axis, and showing two longitudinally-extending, laterally-spaced guide grooves formed on the underside of the upper deck near the head end adjacent to the two sides of the upper deck for receiving rim portions of a pair of wheels rotatably mounted on said pivot pins, and further showing a pair of rollers mounted to the underside of the upper deck near the head end adjacent to the two sides of the upper deck by a pair of downwardly-projecting brackets for reception in a pair of outwardly-opening channels formed in the outer rectangular frame.
Figure 10:
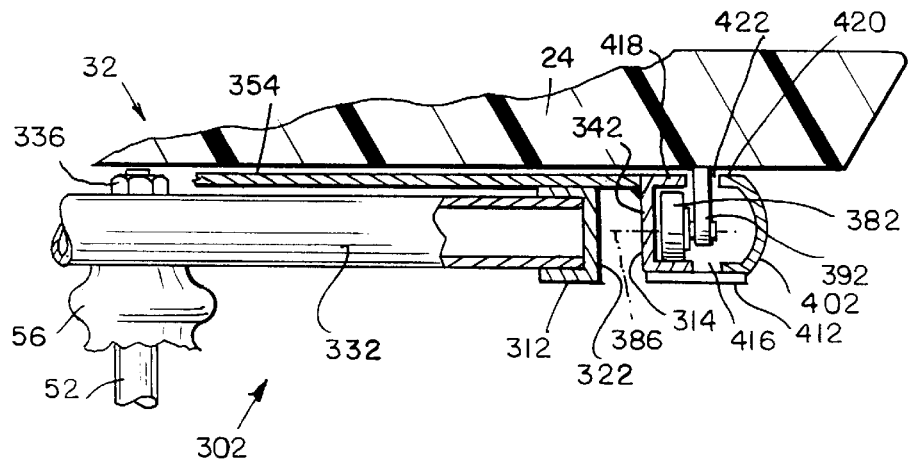
FIG. 10 is a sectional view taken along the line 10—10 in FIG. 9 of the head end of the upper deck, and showing the two generally rectangular nested frames, a roller coupled to the underside of the upper deck and received in an outwardly-opening channel formed in the outer rectangular frame, the head end hydraulic cylinder coupled to a cross member of the inner rectangular frame by a nut and bolt assembly.

As shown in FIGS. 9 and 10, the head end support assembly 302 includes a generally rectangular inner frame 312 nested inside a generally rectangular outer frame 314. The inner and outer frames 312, 314 are pivotally coupled to each other near their respective foot ends 34 for rotation about a first transversely-extending axis 316. The inner frame 312 includes first and second longitudinally-extending siderails 322, 324 in the form of inwardly-opening channels. The longitudinally-extending siderails 322, 324 are held in laterally spaced apart relationship by a head end cross member 332 in the form of a circular tube and a foot end cross member 334 in the form of a square tube. The head end cross member 332 is rigidly attached to the head end hydraulic cylinder 52 by a nut and bolt assembly 336. The outer frame 314, on the other hand, includes first and second longitudinally-extending siderails 342, 344 in the form of outwardly-opening channels. The longitudinally-extending siderails 342 and 344 are held in laterally spaced apart relationship by a head end cross member 352 in the form of a square tube and a foot end cross member 354 in the form of a rectangular plate mounted on the top side of the outer frame 314. The foot ends 34 of the inner siderails 322, 324 and. the foot ends 34 of the outer siderails 342, 344 are pivotally coupled to each other by pivot pins 358 for rotation about the transversely-extending axis 316. Pivotal coupling of the inner and outer frames 312, 314 allows the upper deck 24 to pivot to a Trendelenburg position shown in FIG. 2 or to a reverse Trendelenburg position shown in FIG. 3.

The underside of the upper deck 24 is formed to include two longitudinally-extending, laterally-spaced guide grooves 362 for receiving rim portions of wheels 372 freely rotatable on the pivot pins 358. The wheels 372 are located between the outer walls of the inner siderails 322, 324 and the inner walls of the outer siderails 342, 344 adjacent to the foot ends 34 of the inner and outer frames 312, 314. The outwardly-opening channels 342, 344 of the outer frame 314 are configured to receive a pair of rollers 382 mounted to the underside of the upper deck 24 for rotation about a second transversely-extending axis 386 by a pair of downwardly-projecting brackets 392. As shown in FIG. 10, a pair of guard members 402 in the form of inwardly-opening channels are coupled to the outwardly-opening channels 342, 344 by plate members 412 mounted on the bottom side thereof to form enclosed tracks 416 for receiving the rollers 382 mounted to the underside of the upper deck 24. The outwardly-facing top edges 418 of the outer channel members 342, 344 and the inwardly-facing top edges 420 of the guard members 402 form longitudinally-extending channels or slots 422 along the two sides of the upper deck 24 for slidably receiving the roller-supporting brackets 392. The reception of the rollers 382 mounted to the underside of the upper deck 24 in the enclosed tracks 416 secures the head end 32 of the upper deck 24 to the base 22, while allowing the upper deck 24 to translate longitudinally relative to the base 22 within a certain limited range.

Figure 11:
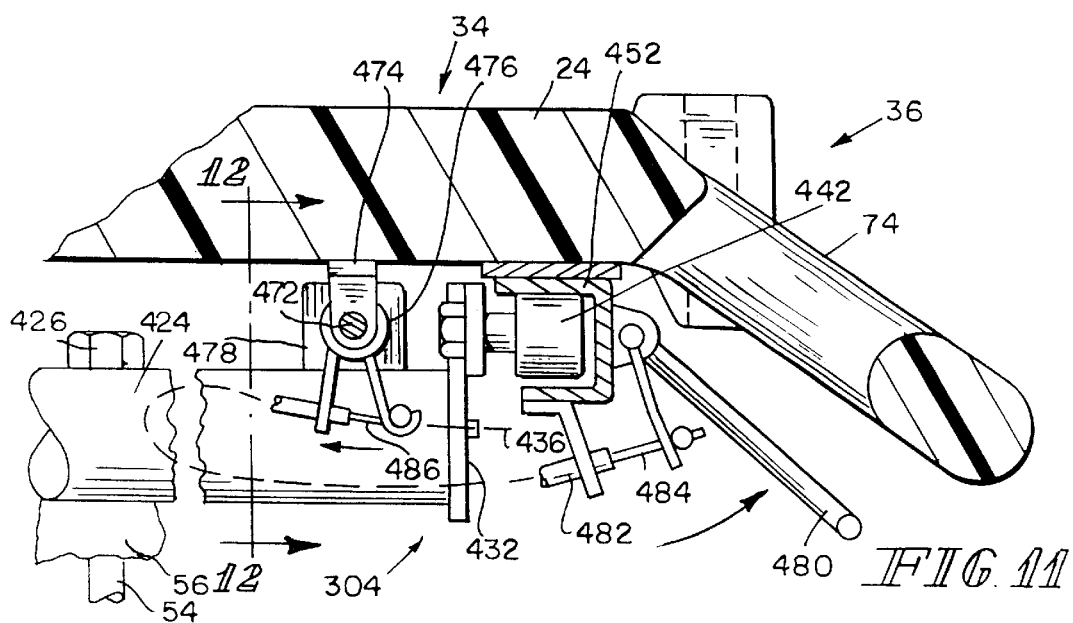
FIG. 11 is a sectional view of a foot end of the upper deck taken along the line 11—11 in FIG. 4, a side handle with a portion broken away, a foot end cross member coupled to the foot end hydraulic cylinder by a nut and bolt assembly, an upwardly-projecting bracket pivotally coupled to one end of the foot end cross member and supporting a pair of rollers, the rollers being configured for reception in an inwardly-opening siderail coupled to the underside of the upper deck near the foot end adjacent to one side thereof for supporting longitudinal movement of the upper deck within a given range, a longitudinally-extending locking rod attached to the underside of the upper deck near the foot end adjacent to said one side, a clamp supported by the foot end cross member and disposed about the locking rod, the clamp normally securely gripping the locking rod to lock the sliding upper deck at a given longitudinal position, a release bar pivotally mounted to the upper deck and coupled to the clamp for freeing the upper deck when actuated to enable the caregiver to adjust the longitudinal position of the upper deck.
Figure 12:
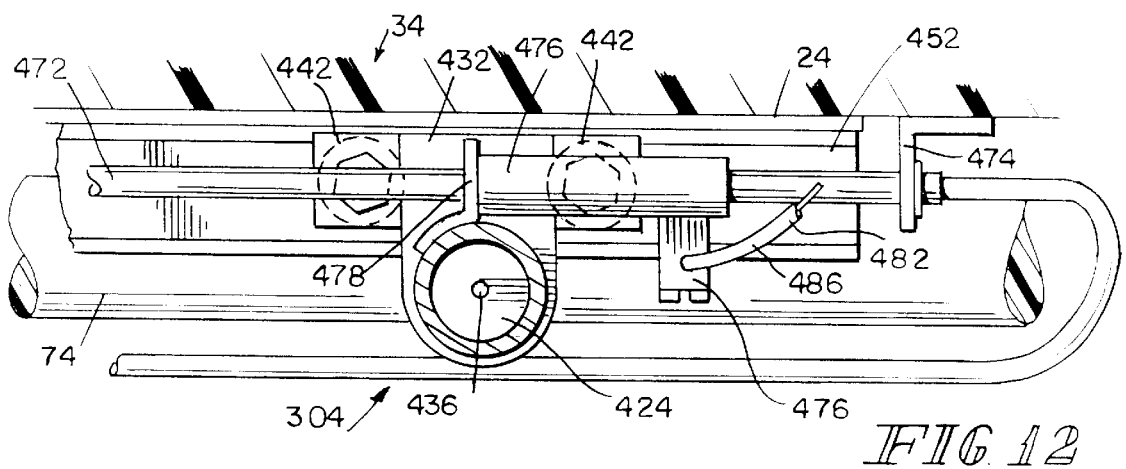
FIG. 12 is a sectional view of the foot end of the upper deck taken along the line 12—12 in FIG. 11, showing the side handle with portions broken away, two rollers in phantom received in the inwardly-opening siderail coupled to the underside of the upper deck near the foot end adjacent to said one side, an upwardly-projecting bracket pivotally coupled to the foot end cross member for supporting the rollers near the foot end of the upper deck, the locking rod fixed to the underside of the upper deck, the clamp disposed about the locking rod, and a cable coupling the release bar to the clamp.

Referring to FIGS. 11 and 12, the foot end support assembly 304 includes a cross member 424 in the form of a circular tube rigidly attached to the foot end hydraulic cylinder 54 by a nut and bolt assembly 426. An upwardly-projecting bracket 432 is pivotally attached to the each end of the tubular cross member 424 for rotation about a third transversely-extending axis 436. Pivotal movement of the brackets 432 relative to the foot end cross member 424 allows the upper deck 24 to pivot to a Trendelenburg position shown in FIG. 2 or to a reverse Trendelenburg position shown in FIG. 3. Each of the brackets 432 supports a pair of rollers 442 configured for reception in the first and second longitudinally-extending, inwardly-opening channels 452 mounted to the underside of the upper deck 24 adjacent to the foot end 34 thereof Reception of the rollers 442 mounted to the cross member 424 in the inwardly opening channels 452 mounted to the underside of the upper deck 24 holds the foot end 34 of the upper deck 24 in place, while allowing the upper deck 24 to translate longitudinally within a predetermined range relative to the base 22.

When the upper deck 24 is horizontal as shown in FIG. 1, a patient's weight is transferred to the rollers 382 near the head end 32 of the stretcher 20, and to the rollers 442 near the foot end 34 of the stretcher 20. The patient's weight on the rollers 382 near the head end 32 of the stretcher 20 is transferred to the outer siderails 342, 344 (urging the outer siderails 342, 344 to rotate about the transversely-extending axis 316 in a clockwise direction 456 shown in FIG. 9), then to the inner frame 312 through the top cross plate 354, and finally to the head end hydraulic cylinder 52 through the head end cross member 332. On the other hand, the patient's weight on the rollers 442 near the foot end 34 of the stretcher 20 is transferred to the foot end cross member 424 through the pivotally-mounted brackets 432, and then to the foot end hydraulic cylinder 54 through the foot end cross member 424.

To move the upper deck 24 to the Trendelenburg position shown in FIG. 2 from the horizontal position shown in FIG. 1, hydraulic pressure in the head end hydraulic cylinder 52 is released by using the head end pressure release pedal 182 coupled to the foot end 34 of the stretcher 20, causing the head end cross member 332 to move down. When the head end cross member 332 moves down, both the inner and outer frames 312 and 314 move down, and the upper deck 24 pivots about the axis 386 of the rollers 382 near the head end 32 of the stretcher 20 and the axis 436 of the pivotally-mounted brackets 432 near the foot end 34 of the stretcher 20. In the Trendelenburg position, a patient's weight is transferred to the rollers 382 near the head end 32 of the stretcher 20, and to the rollers 442 near the foot end 34 of the stretcher 20. The patient's weight on the rollers 382 near the head end 32 of the stretcher 20 is transferred to the outer siderails 342 (urging the outer siderails 342, 344 to rotate about the transversely-extending axis 316 in a clockwise direction 458 in FIG. 2), then to the inner frame 312 through the top cross plate 354, and finally to the head end hydraulic cylinder 52 through the head end cross member 332. On the other hand, the patient's weight on the rollers 442 near the foot end 34 of the stretcher 20 is transferred to the foot end cross member 424 through the pivotally-mounted brackets 432, and to the foot end hydraulic cylinder 54 through the foot end cross member 424.

To move the upper deck 24 to the reverse Trendelenburg position shown in FIG. 3 from the horizontal position shown in FIG. 1, hydraulic pressure in the foot end hydraulic cylinder 54 is released by using the foot end pressure release pedal 184 coupled to the foot end 34 of the stretcher 20 to cause the foot end cross member 424 to move down. When the foot end cross member 422 moves down, the outer frame 314 pivots about the axis 316 of the wheels 372 near the head end 32 of the stretcher 20 in the direction 460 in FIG. 3. The upper deck 24, on the other hand, pivots about the axis 316 of the wheels 72 near the head end 32 of the stretcher 20, and about the axis 436 of the pivotally-mounted brackets 432 near the foot end 34 of the stretcher 20. In the reverse Trendelenburg position, a patient's weight is transferred to the wheels 372 near the head end 32 of the stretcher 20, and to the rollers 442 near the foot end 34 of the stretcher 20. The patient's weight on the wheels 372 near the head end 32 of the stretcher 20 is transferred to the inner frame 312 through the pivot pins 358, and then to the head end hydraulic cylinder 52 through the head end cross member 332. On the other hand, the patient's weight on the rollers 442 near the foot end 34 of the stretcher 20 is transferred to the foot end cross member 424 through the pivotally-mounted brackets 432, and then to the foot end hydraulic cylinder 54 through the foot end cross member 424.

Thus, the novel configuration of the head end and foot end support assemblies 302 and 304 allows the upper deck 24 to move toward the foot end 34 of the stretcher 20, so that a C-Arm 42 can be positioned anyplace from the neck to the tailbone of a patient supported on the deck 24, or tilted about a tranversely-extending axis as shown in FIG. 13, or rotated about a longitudinally-extending axis as shown in FIG. 14 without any obstruction and without the necessity of pulling the C-Arm out from under the patient. The support assemblies 302, 304 also allow the entire upper deck 24 to be raised or lowered as shown in FIG. 1, move the upper deck 24 to a Trendelenburg position as shown in FIG. 2 or to a reverse Trendelenburg position as shown in FIG. 3.

An upper deck locking mechanism 470 is provided for selectively locking the upper deck 24 at a given longitudinal position with respect to the base 22 as shown in FIGS. 11 and 12. The upper deck locking mechanism 470 includes a longitudinally-extending locking rod 472 attached to the underside of the foot end 34 of the upper deck 24 near the first side 36 of the stretcher 20 by means of a pair of downwardly projecting brackets 474. A clamp 476 is disposed about the rod 472, and is secured to the foot end cross member 424 by a bracket 478. The clamp 476 is normally biased to tightly grip the rod 472 to lock the upper deck 24 in place. A upper deck release bar 480 is pivotally mounted to the siderail 452 adjacent to the foot end side handle 64 near the first side 36 of the stretcher 20. The release bar 480 is normally biased in a direction away from the side handle 64. A cable 482 has one end 484 secured to the release bar 480 and a second end 486 secured to the clamp 476. To free the upper deck 60, the release bar 480 is lifted toward the side handle 64. When the release bar 480 is lifted, the end 484 of the cable 482 attached to the release bar 480 is pulled. When the end 484 of the cable 482 is pulled, the second end 486 of the cable 482 secured to the clamp 476 pulls on the clamp 476 to open it up to release the locking rod 472 to, in turn, free the upper deck 24 to move longitudinally relative to the base 22.

Although the invention has been described in detail with reference to a certain preferred embodiment, variations and modifications exist within the scope and spirit of the invention as described and as defined in the following claims.

What is claimed is:

1. A patient support apparatus comprising:

an elongated base having first and second ends, a plurality of casters rotatably mounted to the base, and engaging a floor, an upper deck, first and second actuators coupled to the base adjacent to the first and second ends thereof respectively for movably supporting the upper deck between a low position and a high position, the first actuator controlling a vertical position of a first end of the upper deck and the second actuator controlling a vertical position of a second end of the upper deck, an elongated shaft having a longitudinal axis, the shaft being coupled to the base for rotation about the longitudinal axis between a first orientation and a second orientation, and for movement along the longitudinal axis, a wheel coupled to the shaft for movement relative to the base between a first position spaced apart from the floor when the shaft is rotated to the first orientation, and a second position engaging the floor when the shaft is rotated to the second orientation, and a foot pedal movably mounted to the base adjacent to the second end thereof, the foot pedal being configured to engage a portion of the shaft adjacent to the second end of the base to move the shaft toward the first end and cause the first actuator to adjust the vertical position of the first end of the upper deck.

2. The apparatus of claim 1, wherein the first and second ends of the base correspond to a head end and a foot end thereof, wherein the first and second actuators correspond to a head end actuator and a foot end actuator, and wherein the foot pedal is movably mounted to the base adjacent to the foot end thereof, and is configured to engage said portion of the shaft adjacent to the foot end to move the shaft toward the head end and cause the head end actuator to lower the head end of the upper deck.

3. The apparatus of claim 2, wherein actuators are hydraulic cylinders, wherein the apparatus further includes a foot pump pedal movably mounted to the base adjacent to the foot end thereof, and coupled to the hydraulic cylinders for pumping fluid into the respective hydraulic cylinders for raising the upper deck relative to the base.

4. The apparatus of claim 3, wherein the head end hydraulic cylinder includes a pressure release button, and wherein a portion of the shaft adjacent to the head end of the base is configured to engage said pressure release button when the shaft is moved toward the head end, and release hydraulic pressure in the head end hydraulic cylinder to lower the head end of the upper deck.

5. The apparatus of claim 4, further including a first linkage assembly for selectively coupling the foot pedal to said portion of the shaft adjacent to the foot end.

6. The apparatus of claim 5, wherein the first linkage assembly includes an actuating member having an outwardly-extending, generally horizontal portion, an intermediate base portion and a downwardly-extending, generally vertical portion, wherein the foot pedal is coupled to the free end of the generally horizontal portion, wherein the base portion of the actuating member is pivotally coupled to the foot end of the base, wherein actuation of the foot pedal causes rotation of the downwardly-extending portion of the actuating member, wherein the free end of the downwardly-extending portion is configured to engage said portion of the shaft near the foot end thereof and cause translation of the shaft toward the head end, and wherein translation of the shaft toward the head end causes actuation of the pressure release button to release the pressure in the head end hydraulic cylinder to, in turn, lower the head end of the upper deck.

7. The apparatus of claim 5, wherein the first linkage assembly further includes a transverse plate attached to the shaft adjacent to the foot end, wherein the free end of the downwardly-extending portion is configured to engage said transverse plate and cause translation of the transverse plate and the shaft attached thereto toward the head end, and wherein translation of the shaft toward the head end causes actuation of the pressure release button to release the pressure in the head end hydraulic cylinder to, in turn, lower the head end of the upper deck.

8. The apparatus of claim 7, wherein the first linkage assembly further includes a spring coupled to the shaft to bias the shaft to return to its original position when the foot pedal is released.

9. The apparatus of claim 4, further including a second foot pedal movably mounted to the base adjacent to the foot end thereof, wherein the foot end hydraulic cylinder includes a pressure release button, wherein the second foot pedal is configured to engage the pressure release button coupled to the foot end hydraulic cylinder and release hydraulic pressure in the foot end hydraulic cylinder to lower the foot end of the upper deck.

10. The apparatus of claim 1, further including a brake-steer pedal mounted to the base near the foot end thereof for movement between a brake position and a steer position, and a foot end linkage assembly for coupling the brake-steer pedal to the shaft such that the shaft is moved to the first orientation and the wheel is spaced apart from the floor when the brake-steer pedal is moved to the brake position, and the shaft is moved to the second orientation and the wheel is engaging the floor when the brake-steer pedal is moved to the steer position.

11. The apparatus of claim 10, wherein the shaft has a third neutral position intermediate of the brake and steer positions thereof.

12. The apparatus of claim 10, wherein the foot end linkage assembly includes a cross shaft rotatably coupled to the foot end of the base, the cross shaft supporting a brake-steer pedal adjacent to each end thereof, the foot end linkage assembly further including a bent link fixed to the cross shaft, a connecting link having one end pivotally coupled to the bent link and a second end pivotally coupled to a short link fixed to the foot end of the shaft, wherein rotation of the brake-steer pedal to the brake position causes the shaft to rotate to the first orientation and lift the wheel off the floor, and wherein rotation of the brake-steer pedal to the steer position causes the shaft to rotate to the second orientation and lower the wheel to engage the floor.

13. The apparatus of claim 1, further including a steering wheel support assembly to couple the shaft to the wheel, wherein the steering wheel support assembly includes a bracket supporting the wheel and pivotally coupled to the base for movement between a first position where the wheel is spaced apart from the floor and a second position where the wheel is engaging the floor, a spring biasing the bracket to the first position where the wheel is spaced apart from the floor, and a cam fixed to the shaft and configured to engage the bracket to cause movement of the bracket to the second position where the wheel is engaging the floor when the shaft is rotated to the second orientation.

14. A patient support apparatus comprising:

an elongated base having first and second ends, an upper deck, first and second actuators coupled to the base adjacent to the first and second ends respectively for movably supporting the upper deck between a low position and a high position, the first actuator controlling a vertical position of a first end of the upper deck and the second actuator controlling a vertical position of a second end of the upper deck, an elongated shaft having a longitudinal axis, the shaft being coupled to the base for movement along the longitudinal axis, and a foot pedal movably mounted to the base adjacent to the second end thereof, the foot pedal being configured to engage a portion of the shaft adjacent to the second end of the base to move the shaft toward the first end and cause the first actuator to adjust the vertical position of the first end of the upper deck.

15. The apparatus of claim 14, wherein the shaft is coupled to the base for rotation about the longitudinal axis between a first orientation and a second orientation, wherein the apparatus further includes a plurality of casters rotatably mounted to the base and engaging a floor, and a wheel coupled to the shaft for movement relative to the base between a first position spaced apart from the floor when the shaft is rotated to the first orientation, and a second position engaging the floor when the shaft is rotated to the second orientation.

16. The apparatus of claim 15, further including a steering wheel support assembly to couple the shaft to the wheel, wherein the steering wheel support assembly includes a bracket supporting the wheel and pivotally coupled to the base for movement between a first position where the wheel is spaced apart from the floor and a second position where the wheel is engaging the floor, a spring biasing the bracket to the first position where the wheel is spaced apart from the floor, and a cam fixed to the shaft and configured to engage the bracket to cause movement of the bracket to the second position where the wheel is engaging the floor when the shaft is rotated to the second orientation.

* * * * *